(12) United States Patent
Courtin et al.

(10) Patent No.: US 6,864,233 B2
(45) Date of Patent: Mar. 8, 2005

(54) FUNGICIDAL ECHINOCANDIN DERIVATIVES AND THEIR PREPARATION

(75) Inventors: Olivier Courtin, Paris (FR); Arlette Dussarat, Romainville (FR); Dominique Melon Manguer, Montreuil (FR); Laurent Schio, Bondy (FR)

(73) Assignee: Aventis Pharma S.A. (FR)

( * ) Notice: Subject to any disclaimer, the term of this patent is extended or adjusted under 35 U.S.C. 154(b) by 167 days.

(21) Appl. No.: 10/220,829

(22) PCT Filed: Feb. 14, 2001

(86) PCT No.: PCT/FR01/00419

§ 371 (c)(1),
(2), (4) Date: Dec. 3, 2002

(87) PCT Pub. No.: WO01/60845

PCT Pub. Date: Aug. 23, 2001

(65) Prior Publication Data

US 2004/0014602 A1 Jan. 22, 2004

(30) Foreign Application Priority Data

Feb. 15, 2000 (FR) .............................. 00 01844

(51) Int. Cl.[7] ........................... C07K 7/50; A61K 38/12
(52) U.S. Cl. ........................... 514/9; 530/300; 530/317; 530/333; 514/2; 514/11
(58) Field of Search ................... 514/2, 9, 11; 530/317, 530/333, 338, 343, 332

(56) References Cited

U.S. PATENT DOCUMENTS 5,541,160 A * 7/1996 Balkovec et al. ............. 514/11

FOREIGN PATENT DOCUMENTS

| JP | 5202096 | 8/1993 |
|---|---|---|
| WO | 9527074 | 10/1995 |

OTHER PUBLICATIONS

FA Bouffard, et al. Synthesis and antifungal activity of novel cationic pneumocandin B0 derivatives. (1994) Journal of Medicinal Chemistry, 37, 222–225.*
Roy et al, "Mulundocandin . . . Antibiotic", Journal of Antibiotics, JP, Japan, Antibiotics Research Association, Tokyo, vol. 40, No. 3, Mar. 3, 1987, pp. 275–280.

* cited by examiner

Primary Examiner—Bruce R. Campbell
Assistant Examiner—Andrew D. Kosar
(74) Attorney, Agent, or Firm—Muserlian, Lucas and Mercanti

(57) ABSTRACT

The invention concerns compounds of general formula (I) wherein: $R_1$ represents a hydrogen atom, a hydroxy radical, Ob or Ncd; A represents an oxygen atom, a $CH_2$ radical or a NH radical; B represents the radical of a steroid; $R_3$ represents a hydrogen atom, a methyl or hydroxyl radical; $R_4$ represents a hydrogen atom or a hydroxyl radical; T represents a hydrogen atom, a methyl radical, a $CH_1CONH_2$, $CH_2C\equiv N$ radical, a $(CH_2)_2NH_2$ or $(CH_2)2Nalk^+X^-$ radical; X being a halogen atom and alc an alkyl radical; Y represents a hydrogen atom, a hydroxyl radical or a halogen atom or a $OSO_3H$ radical; W represents a hydrogen atom or a OH radical; Z represents a hydrogen atom or a methyl radical. The compounds of formula (I) exhibit antifungal properties.

15 Claims, No Drawings

FUNGICIDAL ECHINOCANDIN DERIVATIVES AND THEIR PREPARATION

The present invention relates to new derivatives of echinocandin, their preparation process and their use as fungicides.

BRIEF DESCRIPTION OF THE DRAWINGS

A subject of the invention is the compounds of general formula (I):

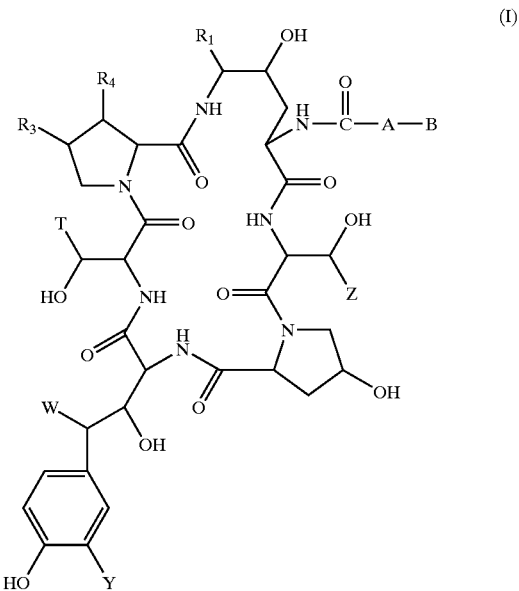

in which:
$R_1$ represents a hydrogen atom,
a hydroxy radical,
an Ob radical, b representing an alkyl, alkenyl or alkynyl radical containing up to 12 carbon atoms, optionally substituted by a halogen atom, an

radical,
b' and b" identical to or different from one another represent a hydrogen atom, an alkyl radical containing up to 12 carbon atoms or an optionally substituted aryl radical, or an

radical in which:
c and d identical to or different from one another, represent a hydrogen atom, a linear, branched or cyclic alkyl radical containing up to 8 carbon atoms, optionally interrupted by an oxygen atom optionally substituted by a halogen atom, an OH radical, an

radical
$c_1$ and $d_1$ representing a hydrogen atom or an alkyl radical containing up to 8 carbon atoms, $c_1$ and $d_1$ being optionally able to form with the nitrogen atom a heterocycle optionally containing one or more additional heteroatoms,
A represents an oxygen atom, a $CH_2$ radical or an NH radical,
B represents the remainder of a steroid,
$R_3$ represents a hydrogen atom, a methyl or hydroxyl radical,
$R_4$ represents a hydrogen atom or a hydroxyl radical,
T represents a hydrogen atom, a methyl radical, a $CH_2CONH_2$, $CH_2C\equiv N$ radical, a $(CH_2)_2NH_2$ or $(CH_2)_2Nalk^+X^-$ radical, X being a halogen atom and alk an alkyl radical containing up to 8 carbon atoms,
Y represents a hydrogen atom, a hydroxyl radical or a halogen atom or an $OSO_3H$ radical or one of the salts of this radical,
W represents a hydrogen atom or an OH radical,
Z represents a hydrogen atom or a methyl radical, as well as the addition salts with acids of the products of formula (I).

Among the addition salts with acids, there can be mentioned those formed with mineral acids, such as hydrochloric, hydrobromic, sulphuric or phosphoric acids or with organic acids such as formic, acetic, trifluoroacetic, propionic, benzoic, maleic, fumaric, succinic, tartaric,

DETAILED DESCRIPTION OF THE INVENTION citric, oxalic, glyoxylic, aspartic acids, alkanesulphonic, such as methane or ethane sulphonic acids, arylsulphonic such as benzene or paratoluenesulphonic acids.
In the definition of the substituents,
the alkyl, alkenyl or alkynyl radical is preferably a methyl, ethyl, propyl, isopropyl, n-butyl, isobutyl, terbutyl, decyl or dodecyl, vinyl, allyl, ethynyl, propynyl, cyclobutyl, cyclopentyl or cyclohexyl radical,
the halogen is preferably fluorine or chlorine, or bromine,
the aryl radical is preferably the phenyl radical.
Among the preferred compounds of the invention, there can be mentioned the compounds of formula (I) in which T represents a hydrogen atom, those in which Y represents a hydrogen atom, those in which Z represents a methyl radical, those in which $R_3$ represents a methyl radical, those in which $R_4$ represents a hydroxyl radical, those in which $R_1$ represents a hydroxyl radical, those in which A represents an oxygen atom, those in which A represents a $CH_2$ radical.
Among the preferred values of B, the following radicals can be mentioned:

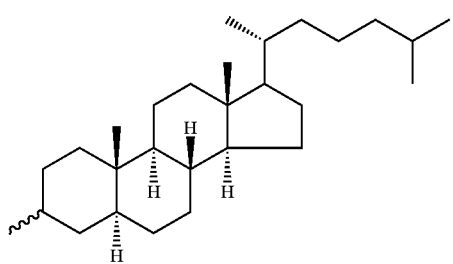

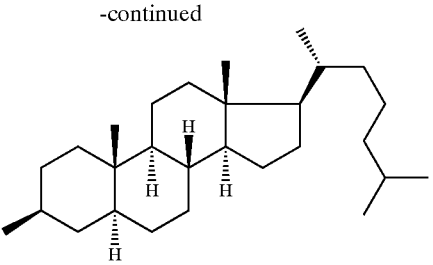

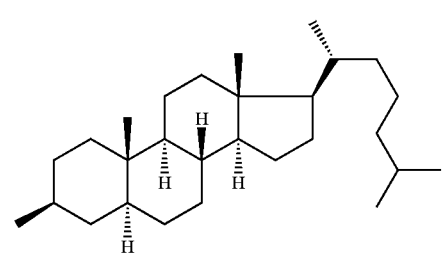

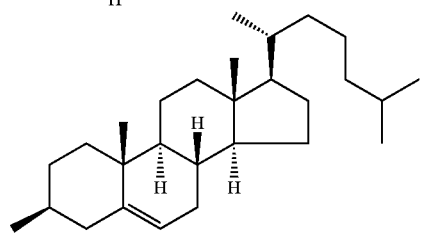

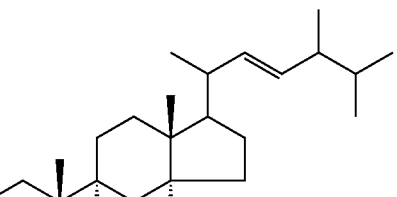

and quite especially the compounds in which B represents a

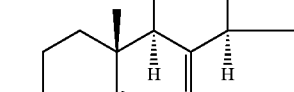

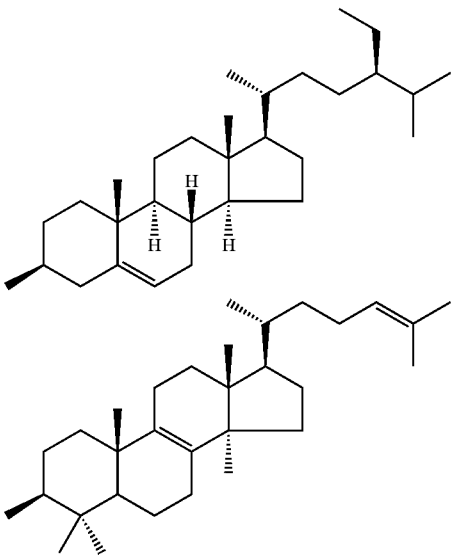

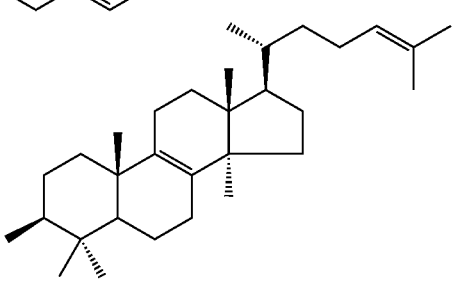

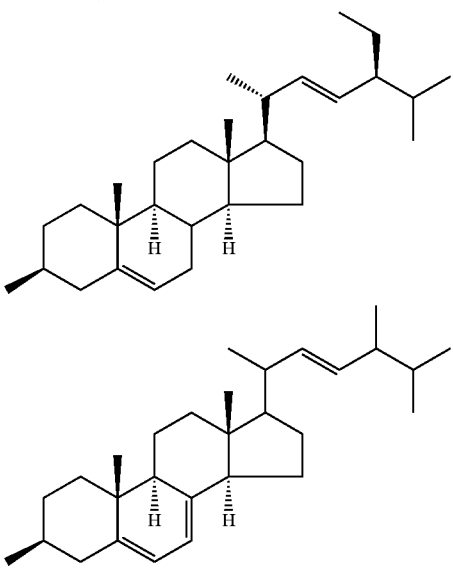

radical.

A quite particular subject of the invention is the compounds the preparation of which is given hereafter in the experimental part and quite especially the compounds of Examples 1, 2 and 3.

The compounds of formula (I) have useful antifungal properties; they are in particular active on *Candida albicans* and other Candida such as *Candida glabrata*, krusei, tropicalis, pseudotropicalis, parapsilosis and *Aspergillus fumigatus, Aspergillus flavus, Cryptococcus neoformans.*

The compounds of formula (I) can be used as medicaments in man or animals, in particular to combat digestive, urinary, vaginal or cutaneous candidosis, cryptococcosis, for example neuromeningeal, pulmonary or cutaneous cryptococcosis, bronchopulmonary and pulmonary aspergillosis and invasive aspergillosis in the immunosuppressed.

The compounds of the invention can also be used in the prevention of mycotic illnesses in the congenital or acquired immunosuppressed.

The compounds of the invention are not limited to a pharmaceutical use, they can also be used as fungicides in fields other than the pharmaceutical field.

Therefore a subject of the invention is, as antifungal compounds, the compounds of formula (I).

A subject of the invention is also the compounds of formula (I), as medicaments.

A quite particular subject of the invention is the pharmaceutical compositions containing as active ingredient at least one compound of formula (I) or one of its salts.

These compositions can be administered by buccal, rectal, parenteral route or by local route as a topical application on the skin and mucous membranes, but the preferred route is the buccal route.

They can be solid or liquid and can be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient or ingredients can be incorporated in the excipients usually used in these pharmaceutical compositions, such as talc, gum arabic, lactose, starch, magnesium stearate, cocoa butter, aqueous or non-aqueous vehicles, fatty matter of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example sterile apyrogenic water.

The dose administered is variable according to the illness treated, the patient in question, the administration route and the product considered. It can be, for example, comprised between 50 mg and 300 mg per day by oral route, in adults for the products of the Examples 1, 2 and 3.

A subject of the invention is also a process for the preparation of the compounds of formula (I), characterized in that a compound of formula (II):

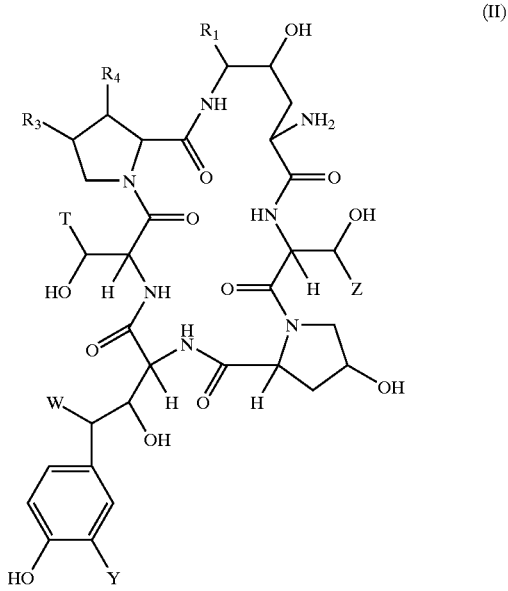

is subjected to the action of a steroid BOH or one of its derivatives in the presence of an activator of the alcohol function, or of a corresponding acid or of one of its derivatives, in order to obtain the corresponding compound of formula (I).

The compounds of formula (II) used as starting product are known products described for example in the European Patent Application 2772028.

In a preferred embodiment of the process of the invention compound (II) is reacted with an alcohol the alcohol function of which is activated, for example using diphosgene or an acid the acid function of which is activated for example using an alkyl chloroformate, as will be explained in detail hereafter in the experimental part.

The Following Examples Illustrate the Invention.

EXAMPLE 1

1-[(4R,5R)-4,5-dihydroxy-N2-[[[(3β, 22E)-ergosta-5,7,22-trien-3-yl]oxy]carbonyl]-L-ornithine]-deoxymulundocandin, Stage A:

176 μl of triethylamine is added to a solution containing 500 mg of ergosterol and 10 ml of methylene chloride. 152 μl of diphosgene in solution in 200 μl of methylene chloride is then added at −20° C. The reaction mixture is maintained under agitation for 3 hours at a temperature comprised between 0 and 10° C. The product obtained is brought to dryness.

Stage B:

The product prepared in Stage A is introduced at −5° C. into a mixture containing 627.3 mg of deoxymulundocandin nucleus, 30 ml of dioxane, 109.4 mg of sodium acid carbonate and 2.3 ml of demineralized water. The reaction mixture is maintained under agitation for 18 hours, then concentrated under reduced pressure. The product obtained is chromatographed on silica eluting with a methylene chloride/methanol/water mixture (86-13-1). 73 mg of product is obtained which is taken up in ether in the presence of a few drops of ethyl acetate, followed by separating, washing with ether and drying. 69 mg of product is obtained which is taken up in a minimum amount of water, followed by triturating, separating and washing with water and with ether. After drying 31.2 mg of product is obtained. TLC ($CH_2Cl_2/CH_3OH/H_2O$: 86-13-1) Rf=0.12.

Mass spectrum:

$MNa^+=1212^+$ $MH^+=293^+$

| Residue | δppm1H | δppm13C |
|---|---|---|
| A | Threonine | (Thr) |
| NH | 8.08 | — |
| C=O | — | 169.4 |
| CHα | 4.78 | 56.2 |
| HO—CHβ | 4.51 | 64.7 |
| $CH_3\gamma$ | 1.02 | 19.3 |
| B | γHydroxy proline | (OH Pro) |
| N | — | — |
| C=O | — | 170.9 |
| CHα | 4.31 | 60.9 |
| $CH_2\beta$ | 1.92–2.19 | 37.1 |
| HO—CHγ | 4.40 | 68.9 |
| $NCH_2\delta$ | 4.16–3.60 | 55.4 |
| C | βHydroxy homo tyrosine | (hTyr) |
| NH | 7.59 | — |
| C=O | — | 169.2 |
| CHα | 4.21 | 55.6 |
| HO—CHβ | 4.09 | 72.5 |
| $CH_2\gamma$ | 2.48–2.57 | 38.7 |
| C1 | — | 128.1 |
| C2–6 | 6.94 | 129.8 |
| C3–5 | 6.64 | 114.4 |
| C4 | — | 155.1 |

-continued

| Residue | δppm1H | δppm13C |
|---|---|---|
| OH | 9.12 | — |
| D | Serine | (Ser) |
| NH | 7.30 | — |
| C=O | — | 167.8 |
| CHα | 4.85 | 51.5 |
| HO—CH₂β | 3.45–3.57 | 62.0 |
| E | βHydroxy γmethyl proline | (OH Me Pro) |
| N— | — | — |
| C=O | — | 168.4 |
| CHα | 4.16 | 68.6 |
| HO—CHβ | 3.99 | 73.6 |
| CHγ | 2.34 | 36.7 |
| CH₃δ | 0.98 | 10.4 |
| NCH₂δ | 3.23–3.91 | 50.8 |
| F/F' | Ornithine | (Orn) |
| F  NH | 7.79 | — |
| HO—CHα | 5.10 | 71.4 |
| HO—CHβ | 3.83 | 69.2 |
| F'  NH | 7.17 | — |
| C=O | — | 171.5 |
| CHα | 3.86 | 51.3 |
| CH₂β | 1.68–1.82 | 33.9 |
| S | $^1$H | $^{13}$C |
| 3 | 4.34 | 71.7 |
| 4 | 2.26–2.50 | 36.4 |
| 6 | 5.54 | 119.3 |
| 7 | 5.34 | 115.8 |
| 9 | 1.93 | 45.2 |
| 14 | 1.87 | 53.6 |
| 17 | 1.26 | 54.8 |
| 18Me | 0.58 | 11.6 |
| 19Me | 0.90 | 15.5 or 17.0 |
| 20 | 2.02 | 39.5 |
| 21 | 1.01 | 20.5 |
| 22 | 5.21 | 135.0 |
| 23 | 5.22 | 131.2 |
| 24 | 1.83 | 41.7 |
| 25 | 1.46 | 32.1 |
| 26 | 0.81 | 19.3 |
| 27 | 0.81 | 19.3 |
| 28 | 0.89 | 15.5 or 17.0 |
| The other CH₂'s | 1.65–1.58 | 20.1 |
|  | 1.61–1.29 | 22.1 |
|  | 1.71–1.27 | 27.5 |
|  | 1.81–1.50 | 27.9 |
|  | 1.83–1.28 | 37.2 |
|  | 2.01–1.23 | 38.2 |

EXAMPLE 2

1-[(4R,5R)-4,5-dihydroxy-N2-[[[(3β)-lanosta-8,24-dien-3-yl]oxy]carbonyl]-L-ornithine]-deoxymulundocandin, Stage A:

73 μl of diphosgene and 84 μl of triethylamine are introduced into a solution containing 256 mg of lanosterol and 4.6 ml of methylene chloride.

Stage B:

50.49 mg of sodium acid carbonate and 1.1 ml of water are introduced into a mixture of 238 mg of deoxymulundocandin and 19 ml of dioxane. The reaction medium is cooled down to −5° C., the product prepared in Stage A is introduced, followed by agitating for 10 minutes at −5° C. and leaving the temperature to return to ambient temperature. Agitation is carried out for 15 hours at ambient temperature, then the product obtained is chromatographed $CH_2Cl_2/CH_3OH/H_2O$ (86-13-1). 75 mg of product is obtained which is chromatographed on silica eluting with a methylene chloride/methanol/water mixture (84-15-1). 41.7 mg of product is obtained. Mass spectrum: MNa$^+$=1242.5

EXAMPLE 3

1-[(4R,5R)-4,5-dihydroxy-N2-[[[(3β, 22E)-ergosta-5,7,22-trien-3-yl]oxy]carbonyl]-L-ornithine]-mulundocandin, Stage A:

95 μl of triethylamine is added to a solution containing 224 mg of ergosterol and 7 ml of methylene chloride. The solution obtained is cooled down to −5° C. and 75 μl of trichloromethylchloroformate is added. The suspension is agitated at [0° C.+5° C.] for 3 hours, followed by bringing to dryness under reduced pressure and leaving for one hour under vacuum. A product is obtained which is used as it is in Stage B.

Stage B:

A suspension containing 250 mg of mulundocandin nucleus and 20 ml of dioxane is agitated for 30 minutes. 59 mg of sodium acid carbonate in solution in 1.5 ml of water is added. The suspension is cooled down to 0° C.+5° C. and the product obtained in Stage A is added. The reaction medium is left to return to ambient temperature and agitated for 20 hours, followed by bringing to dryness under reduced pressure, taking up in 5 ml of ethyl acetate, triturating and separating. 125 mg of product is obtained which is chromatographed on silica eluting with a methylene chloride/methanol/water mixture (79-20-1). In this way the sought product is obtained.

Mass spectrum MS: 1228 MNa$^+$

| Residue | δppm1H | δppm13C |
|---|---|---|
| A | Threonine | (Thr) |
| NH | 7.96 | — |
| C=O | — | 169.9 |
| CHα | 4.78 | 56.0 |
| HO—CHβ | 4.40 | 65.5 |
| CH₃γ | 1.08 | 19.2 |
| B | γHydroxy proline | (OH Pro) |
| N | — | — |
| C=O | — | 170.2 |
| CHα | 4.31 | 60.5 |
| CH₂β | 1.86–2.18 | 36.9 |
| HO—CHγ | 4.40 | 68.9 |
| NCH₂δ | 3.66–3.90 | 55.3 |
| C | βHydroxy homo tyrosine | (hTyr) |
| NH | 7.33 | — |
| C=O | — | 169.3 |
| CHα | 4.03 | 53.4 |
| HO—CHβ | 3.98 | 74.9 |
| HO—CHγ | 4.21 | 72.9 |
| C1 | — | 132.2 |
| C2–6 | 7.02 | 127.7 |
| C3–5 | 6.66 | 114.4 |
| C4 | — | 156.3 |
| OH | 9.23 | — |
| D | Serine | (Ser) |
| NH | 7.29 | — |
| C=O | — | 167.9 |

-continued

| Residue | δppm1H | δppm13C |
|---|---|---|
| CHα | 4.80 | 51.8 |
| HO—CH₂β | 3.52 | 62.1 |
| E | βHydroxy γmethyl proline | (OH Me Pro) |
| N | — | — |
| C=O | — | 168.4 |
| CHα | 4.18 | 68.5 |
| HO—CHβ | 3.99 | 73.4 |
| CHγ | 2.34 | 36.6 |
| CH₃δ | 0.96 | 10.5 |
| NCH₂δ | 3.20–3.90 | 50.8 |
| F/F' | Ornithine | (Orn) |
| F NH | 7.82 | — |
| HO—CHα | 5.08 | 71.7 |
| HO—CHβ | 3.80 | 69.0 |
| F' NH | 7.18 | — |
| C=O | — | — |
| CHα | 3.89 | 51.5 |
| CH₂β | 1.82–1.68 | 34.1 |
| R | $^1$H | $^{13}$C |
| C=O | — | — |
| 1 | — | — |
| 2 | — | — |
| 3 | 4.35 | 71.7 |
| 4 | 2.27–2.50 | 36.4 |
| 5 | — | 138.5 |
| 6 | 5.54 | 119.4 |
| 7 | 5.34 | 115.8 |
| 8 | — | 146.3 |
| 9 | 1.95 | 45.2 |
| 10 | — | — |
| 11 | 1.26 | 21.7 |
| 12 | 2.02 | 38.1 |
| 13 | — | 42.1 |
| 14 | 1.89 | 53.5 |
| 15 | — | — |
| 16 | — | — |
| 17 | 1.29 | 54.7 |
| 18Me | 0.60 | 11.4 |
| 19Me | 0.89 | 15.4 |
| 20 | 2.04 | 39.5 |
| 21Me | 1.01 | 20.7 |
| 22 | 5.21 | 135.0 |
| 23 | 5.23 | 131.0 |
| 24 | 1.87 | 41.7 |
| 25 | 1.48 | 32.1 |
| 26 | 0.80–0.82 | 19.2 |
| 27 | — | — |
| 28 | 0.89 | 16.9 |

EXAMPLE 4

1-[(4R,5R)-4,5-dihydroxy-N2-[[[(3β)-lanosta-8,24-dien-3-y]carbonyl]-L-ornithine]-mulundocandin, By operating as previously starting from 256 mg of lanosterol and 235 mg of deoxymulundocandin nucleus, 45 mg of sought product is obtained.

Mass spectrum: 12580 MNa⁺

EXAMPLE 5

1-[(4R,5R)-4,5-dihydroxy-N2-[[[(3β)-cholest-5-en-3-yl]oxy]carbonyl]-L-ornithine]-mulundocandin, By operating as previously, starting from 233 mg of cholesterol and 250 mg of mulundocandin nucleus, 10 mg of sought product is obtained. MS: MH⁺=1197.3 MNa⁺=1218.0

EXAMPLE 6

1-[(4R,5R)-4,5-dihydroxy-N2-[[[(3β)-cholest-5-en-3-yl]oxy]carbonyl]-L-ornithine]-deoxymulundocandin, By operating as in Example 1, starting from 233 mg of cholesterol and 250 mg of deoxymulundocandin, the sought product is obtained. MS: MNa⁺=12202

EXAMPLE 7

1-[(4R,5R)-4,5-dihydroxy-N2-[[[(3β)-cholestan-3-yl]oxy]carbonyl]-L-ornithine]-mulundocandin, By operating as in Example 1, starting from 455 mg of 5α-cholestane-3β-ol, 521 mg of sought product is obtained.

EXAMPLE 8

1-[(4R,5R)-4,5-dihydroxy-N2-[[[(3β)-cholestan-3-yl]oxy]carbonyl]-L-ornithine]-deoxymulundocandin, By operating as in Example 1 starting from 455 mg of 5α-cholestan 3β-ol and 449.93 mg of deoxymulundocandin, 186 mg of sought product is obtained. MS: 1204.4 Da=MNa⁺

EXAMPLE 9

1-[(4R,5R)-4,5-dihydroxy-N2-[[[(3β)-stigmast-5-en-3-yl]oxy]carbonyl]-L-ornithine]-deoxymulundocandin, By operating as in Example 1 starting from 829 mg of β-sitosterol and 1.2 g of deoxymulundocandin nucleus, 99 mg of sought product is obtained. Mass spectrum: 1230 Da=MNa⁺

EXAMPLE 10

1-[(4R,5R)-4,5-dihydroxy-N2-[[[(3β, 22e)-stigmasta-5,22-dien-3-yl]oxy]carbonyl]-L-ornithine]-deoxymulundocandin, By operating as in Example 1 starting from 300 mg of stigmasterol and 395 mg of deoxymulundocandin nucleus, 53 mg of sought product is obtained. Mass spectrum: 1228 Da=MNa⁺

EXAMPLE 11

1-[(4R,5R)-4,5-dihydroxy-N2-[[[(3β)-stigmast-5-en-3-yl]oxy]carbonyl]-L-ornithine]-mulundocandin, By operating as in Example 1, starting from 810 mg of β-sitosterol and 500 mg of mulundocandin nucleus, 330 mg of sought product is obtained. Mass spectrum: 1230 Da=MLi⁺

EXAMPLE 12

1-[(4R,5R)-4,5-dihydroxy-N2-(cholestan-3-ylacetyl)-L-ornithine]-deoxymulundocandin (isomer A) and (isomer B)

44 μl of tributylamine is added to a solution containing 67.8 mg of the product of Preparation P below and a mixture of 1.5 ml of DMF and 1.5 ml of dioxane. The reaction medium is placed in an ice bath and 22 ml of isobutyl chloroformate is added. The reaction mixture is kept in the ice bath for 10 minutes, then for 2 hours at ambient temperature. 100 mg of deoxymulundocandin nucleus is added, followed by maintaining under agitation for 15 hours, concentrating under reduced pressure, taking up in ether, triturating and separating. After washing with ether, 177 mg of product is obtained which is chromatographed on silica eluting with a methylene chloride/methanol/water mixture (86-13-11). 19 mg of isomer A and 47 mg of isomer B are obtained.

Rf=0.47 and Rf=0.43.

Preparation P:

Stage A:

2.47 ml of n-butyllithium in hexane at 15% is added to a solution containing 961 mg of methyl dimethoxyphosphono-acetate and 2 ml of THF. Agitation is carried out for 30 minutes and 500 mg of cholestanone and 2 ml of anhydrous THF are added, followed by agitating for 1 hour, adding 2 ml of water, extracting with ether, washing with water, drying over magnesium sulphate, filtering and bringing to dryness. The residue is taken up in methanol, followed by triturating and separating. 544 mg of sought product is obtained.

Stage B:

523 mg of the product of the preceding stage, 105 mg of 10% palladium on carbon and 20 ml of cyclohexane are maintained under agitation and a hydrogen atmosphere for 15 hours. After filtering and bringing to dryness, 520 mg of product is obtained which is chromatographed on silica eluting with a cyclohexane/ethyl acetate mixture (95-5) then with a cyclohexane/methylene chloride mixture (5/5). A mixture of 2 isomers is obtained. Rf=0.49 and Rf=0.67.

Stage C:

200 µl of caustic soda lye is added to a suspension containing 502 mg of the product of the preceding stage, 2 ml of ethylene glycol. The reaction mixture is taken to reflux for 50 minutes, followed by cooling down to 50° C., acidifying with hydrochloric acid and concentrating. 2.6 ml of water is added, the solution is taken to reflux, followed by separating and washing with water, dissolving the product obtained in methylene chloride, decanting, drying and bringing to dryness. 460 mg of sought product is obtained. Rf=0.34 $CH_2Cl_2$/MEOH (95-5).

EXAMPLE 13

1-[(4R,5R)-4,5-dihydroxy-N2-[[[(3β,22E)-stigmasta-5,22-dien-3-yl]oxy]carbonyl]-L-ornithine]-mulundocandin, By operating as in Example 1, starting from 403 mg of stigmasterol and 400 mg of mulundocandin nucleus, 176 mg of sought product is obtained.

EXAMPLE

Pharmaceutical Composition

Tablets were prepared containing:

| | |
|---|---|
| Product of Example 1 | 150 mg |
| Excipient s.q.f. | 1 g |

(Detail of excipient: starch, talc, magnesium stearate).

PHARMACOLOGICAL STUDY

A—Inhibition of the Glucan Synthase of Candida Albicans.

Candida albicans membranes are purified according to the process described by Tang et al Antimicrob. Agents Chemother 35, 99-103, 1991. 22.5 µg of membrane proteins are incubated in a mixture of 2 mM of $^{14}$C-UDP glucose (specific activity=0.34 mCi./mmol, 50 µg of a α-amylase, 1 mM of dithiotreitol (DTT), 1 mM EDTA, 100 mM NaF, 7 µM of GTP-γ-S, 1M of sucrose and 50 mM of Tris-HCL (pH 7.8) in a volume of 100 µl. The medium is incubated at 25° C. for 1 hour and the reaction is terminated by adding TCA at a final concentration of 5%. The reaction mixture is transferred onto a pre-moistened glass fibre filter. The filter is washed, dried and its radioactivity is counted. Mulundocandin is used as a positive control. Control of the vehicle is carried out with the same quantity of 1% DMSO. The results obtained show that in this test the products of the invention show a good activity in particular the products of Examples 2 and 3.

B—Activity on the *Aspergillus fumigatus* Enzyme.

The enzyme is prepared according to the process of Beaulieu et al.(Antimicrob. Agents Chemother 38, 937-944, 1994).

The protocol used is identical to the protocol described above for the enzyme of *Candida albicans* except that dithiotreitol is not used in the reaction mixture.

In this test the products of the invention show a good activity.

What is claimed is:

1. A compound of the formula:

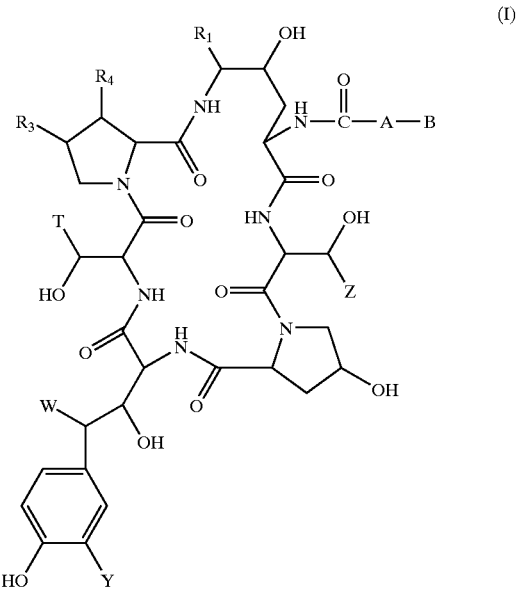

(I)

wherein $R_1$ is selected from the group consisting of hydrogen, hydroxyl, Ob

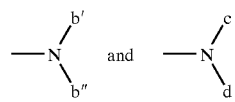

b is selected from the group consisting of alkyl, alkenyl and alkynyl of up to 12 carbon atoms, optionally substituted by halogen;

b' and b" are individually selected from the group consisting of hydrogen, alkyl of up to 12 carbon atoms and unsubstituted or substituted aryl;

c and d are selected from the group consisting of hydrogen, alkyl and cycloalkyl of up to 8 carbon atoms, optionally interrupted by an oxygen atom and unsubstituted or substituted by a member selected from the group consisting of halogen, OH and $$N\begin{matrix}c_1\\d_1\end{matrix}$$

$c_1$ and $d_1$ are hydrogen or alkyl of up to 8 carbon atoms or $c_1$ and $d_1$ form with the nitrogen atom a heterocycle optionally containing at least one heteroatom, A is selected from the group consisting of oxygen, —$CH_2$— and NH, B is a steroid linked at position 3, $R_3$ is selected from the group consisting of hydrogen, methyl and hydroxyl, $R_4$ is hydrogen or hydroxyl, T is selected from the group consisting of hydrogen, methyl, —$CH_2$—$CONH_2$), —$CH_2 \equiv N$, —$(CH_2)_2NH_2$ and —$(CH_2)_2Alk^+X$, X is halogen and Alk is an alkyl of up to 8 carbon atoms, Y is selected from the group consisting of hydrogen, hydroxyl, halogen and —$OSO_2H$ or a salt thereof, W is hydrogen or —OH, Z is hydrogen or methyl and its pharmaceutically acceptable acid addition salts.

2. The compound of claim 1 wherein T is hydrogen.
3. The compound of claim 1 wherein Y is hydrogen.
4. The compound of claim 1 wherein Z is methyl.
5. The compound of claim 1 wherein $R_3$ is methyl.
6. The compound of claim 1 wherein $R_4$ is hydroxyl.
7. The compound of claim 1 wherein $R_1$ is hydroxyl.
8. The compound of claim 1 wherein A is oxygen.
9. The compound of claim 1 wherein A is —$CH_2$—.
10. The compound of claim 1 wherein B is selected from the group consisting of:

and

11. The compound of claim 10 wherein B is:

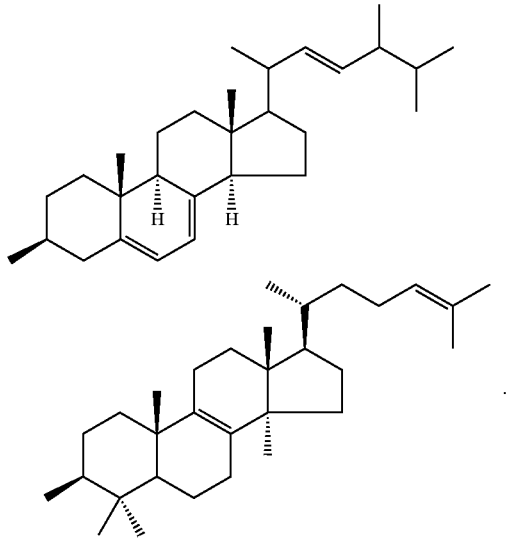

or

12. A compound of claim 1 selected from the group consisting of:

1-[(4R,5-dihydroxy-N2-[[[(3β22E)-ergosta-5,7,22-trien-3-yl]oxy]carbony]-L-ornithine]-mulundocandin, 1-[(4R,5R)-4,5-dihydroxy-N2-[[[3β-lanosta-8,24-dien-3-yl]-L-ornithine]-deoxymulundocandin and 1-[(4R,5R)-4,5-dihyddroxy-N2-[[[(3β,22E)-ergosta-5,7,22-trien-3-yl]oxy]carbonyl]-L-ornithine]-deoxymulundocandin.

13. A process for the preparation of a compound of claim 1 comprising reacting a compound of the formula:

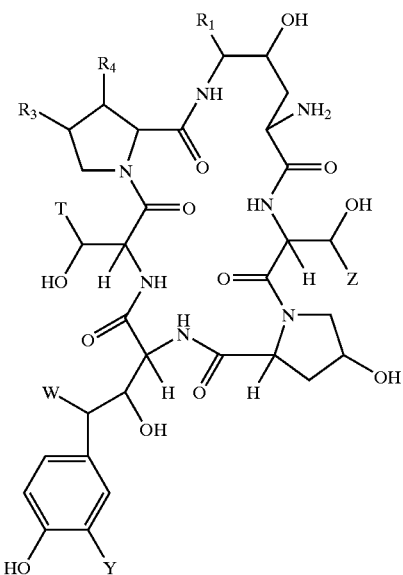

with a steroid BOH where B is defined as in claim 1 or of one of its derivatives in the presence of an activator of the alcohol function, or of a corresponding acid or of one of its derivatives, to obtain the corresponding compound of formula (I).

14. An antifungal composition comprising an antifungicidally effective amount of a compound of claim 1 and an inert carrier.

15. A method of treating fungal infections in warm-blooded animals comprising administering to warm-blooded animals in need thereof an antifungicidally effective amount of a compound of claim 1.

* * * * *